United States Patent
Basile et al.

[11] Patent Number: 5,431,674
[45] Date of Patent: Jul. 11, 1995

[54] COMPOUND MOTION CUTTING DEVICE

[75] Inventors: Peter A. Basile, Lawrenceville; Scott C. Brown, Princeton; George A. Clark, East Windsor, all of N.J.

[73] Assignee: PA Consulting Group, Hightstown, N.J.

[21] Appl. No.: 117,826

[22] Filed: Sep. 7, 1993

[51] Int. Cl.[6] .................................. A61B 17/32
[52] U.S. Cl. ................................ 606/170; 606/174
[58] Field of Search ............... 606/51, 52, 174, 137, 606/170, 167; 30/173, 204; 81/415, 421, 418; 128/750–755

[56] References Cited

U.S. PATENT DOCUMENTS

| | | |
|---|---|---|
| 518,600 | 4/1894 | Hallman . |
| 2,605,543 | 8/1952 | Josselyn . |
| 4,122,856 | 10/1978 | Mosior et al. . |
| 4,165,745 | 8/1979 | Heifetz . |
| 4,545,374 | 10/1985 | Jacobson . |
| 4,696,107 | 9/1987 | Held . |
| 4,712,545 | 12/1987 | Honkanen . |
| 4,763,669 | 8/1988 | Jaeger . |
| 4,887,612 | 12/1989 | Esser et al. ............... 606/174 |
| 4,896,678 | 1/1990 | Ogawa . |
| 5,152,780 | 10/1992 | Honkanen et al. . |
| 5,171,256 | 12/1992 | Smith et al. . |
| 5,201,759 | 4/1993 | Ferzli ......................... 606/170 |
| 5,219,354 | 6/1993 | Choudhury et al. ....... 606/174 |
| 5,254,129 | 10/1993 | Alexander ................. 606/170 |

FOREIGN PATENT DOCUMENTS

| | | |
|---|---|---|
| 050053 | 9/1911 | Austria . |
| 245402 | 4/1912 | Germany . |
| 2904115 | 8/1980 | Germany .................. 606/174 |

*Primary Examiner*—Stephen C. Pellegrino
*Assistant Examiner*—William W. Lewis
*Attorney, Agent, or Firm*—Panitch Schwarze Jacobs & Nadel

[57] ABSTRACT

A compound motion cutting device for cutting a work piece includes a tubular member having first and second ends, a pair of operating members and a drive rod having first and second ends and extending longitudinally into the tubular member. One of the operating members is secured to the first end of the tubular member and the first end of the drive rod is secured to the other of the operating members. An anvil is supported proximate the second end of the tubular member and includes a surface for supporting the work piece and a slot extending through the support surface. A cutting member includes a first end pivotally attached to the second end of the drive rod and a cam slot extending laterally therethrough. A pin is supported proximate the second end of the tubular member an extends through the cam slot in the cutting member. Movement of the operating members relative to each other in one direction causes the drive rod to move the cutting member in a first longitudinal direction and the pin and cutting member cam slot cooperate to simultaneously rotate the cutting member toward the anvil and to extend at least partially into the anvil slot to cut the work piece with a combined longitudinal and rotational slicing motion.

14 Claims, 4 Drawing Sheets

COMPOUND MOTION CUTTING DEVICE

FIELD OF THE INVENTION

The present invention relates generally to cutting instruments and, more particularly, to a compound motion cutting device particularly well adapted for cutting body tissue in areas of limited access.

BACKGROUND OF THE INVENTION

Cutting devices are well known in the art. Such devices (scissors, punches, graspers) are generally used in surgery to cut through body tissue in areas of limited access. Conventional surgical scissors are limited by the singular rotational motion of the blades allowing only a shearing action to cut tissue. As a result, there is a tendency for tissue to roll due to the separation of the scissor blades. The blade separation thus impedes cutting and can lead to tissue tearing.

Efforts have been made to solve the aforementioned problems by producing surgical scissors which use a preload on the blades to prevent tissue roll induced by blade separation. The force required to overcome such preloads is frequently greater than the force required to perform a cut. This causes tactile feedback from the actual cutting to fall well below the perception threshold of a surgeon or other user.

Another disadvantage of conventional surgical scissors is that the blades rub against each other resulting in metal against metal blade edge wear. As a result, over time, the blades get dull and must be sharpened or discarded. Efforts have also been made to solve the wear problem of conventional surgical scissor parts by increasing the dimensions of selected parts of the surgical scissors to increase part strengths. However, such efforts have been wholly unsuccessful, in as much as the increased dimensions tend to render the instruments less satisfactory for use in confined spaces.

The present invention overcomes many of the disadvantages inherent in the above-described prior art surgical cutting devices by providing a compound motion cutting device designed to effect a cutting action which is a combination of shearing and cutting, rather than shearing alone, resulting in a slicing motion that more closely approximates the motion of a surgeon's scalpel. The present invention employs a single blade compound motion cutting device including an anvil having a support surface for a work piece with a slot which provides clearance for the blade so that rolling of the work piece as it is being cut is prevented and blade edge wear is avoided to maintain blade sharpness.

The compound motion cutting device of the present invention offers significant improvement in tactile feedback over conventional cutting devices by minimizing blade preload and lowering frictional forces found in conventional steel against steel blades with equal preload. The cutting device of the present invention employs parts which are relatively small in size and are able to function well in confined areas of limited access.

SUMMARY OF THE INVENTION

Briefly stated, the present invention comprises a compound motion cutting device including a tubular member having first and second ends and a pair of operating members movable relative to each other. One of the operating members is secured to the first end of the tubular member. A drive rod having first and second ends extends longitudinally into the tubular member. The first end of the rod is secured to the other of the operating members such that movement of the operating members relative to each other causes the rod to move longitudinally within the tubular member. An anvil is supported proximate the second end of the tubular member and has a surface for supporting a work piece and a slot extending through the support surface. A cutting member has first and second ends and includes a cam slot extending laterally therethrough. The first end of the cutting member is pivotally attached to the second end of the drive rod and the cutting member is aligned with the anvil slot. A pin is supported proximate to the second end of the tubular member and extends through the cam slot in the cutting member. Movement of the operating members relative to each other in one direction causes the drive rod to move in a first longitudinal direction within the tubular member toward the operating members. The movement of the drive rod in the first direction causes the cutting member to move in the first direction, the pin and the cutting member cam slot cooperating to cause the cutting member to simultaneously rotate toward the anvil and to extend at least partially into the anvil slot to cut the work piece with a combined longitudinal and rotational slicing motion.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF PREFERRED EMBODIMENTS

While this invention is susceptible of embodiments in many different forms, this specification and the accompanying drawings disclose only some specific forms as examples of the use of the invention. The invention is not intended to be limited to the embodiment so described, and the scope of the invention will be pointed out in the appended claims.

Figure 1:
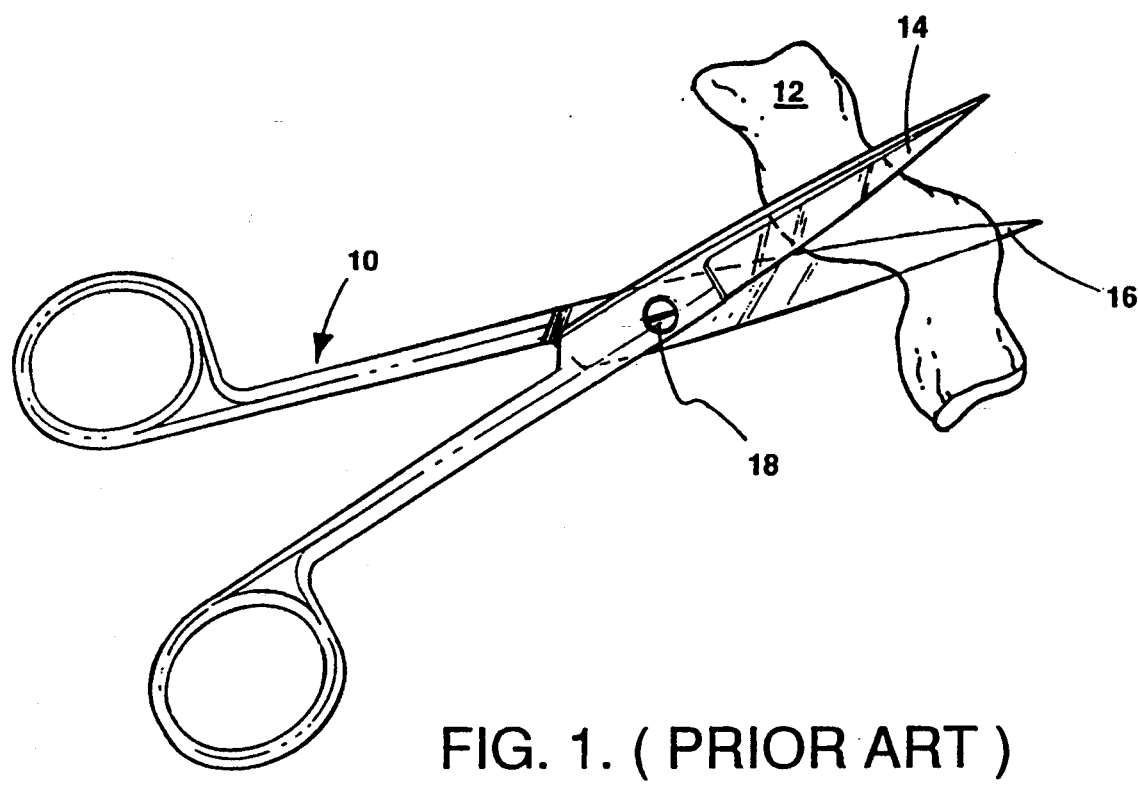
FIG. 1 is a perspective view of a conventional prior art surgical cutting device.
Figure 1A:
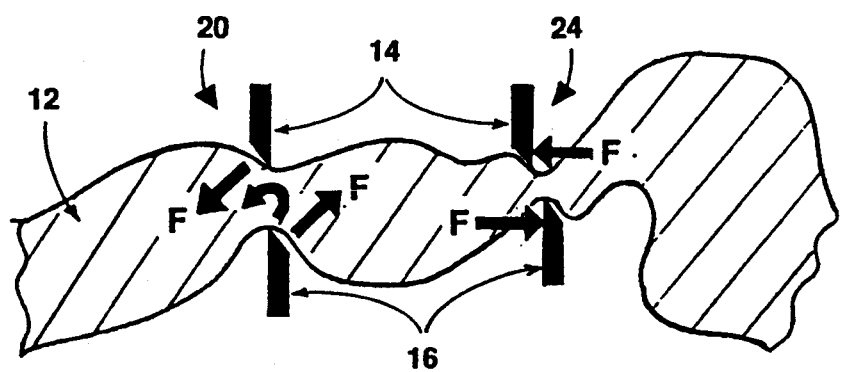
FIG. 1A illustrates rolling of a work piece and blade separation as a result of cutting the work piece with the prior art cutting device of FIG. 1.

Referring now to the drawings in detail, wherein like numerals are used to indicate like elements throughout, there is shown in FIGS. 1 and 1A is a prior art surgical cutting device, generally designated at 10, for cutting a work piece 12. The prior art cutting device 10 includes blades 14, 16 connected at a pivot point 18.

In discussing the prior art cutting device (FIGS. 1, 1A) and the preferred embodiment of the present invention described below, the work piece 12 refers to body tissue, such as vessels, cartilage, or a portion of an organ. The types of work pieces cut by surgical and non-surgical cutting instruments, however, are well known by those skilled in the art. Accordingly, the subject matter which is to be cut is herein referred to only as a work piece and any further description thereof is omitted for purposes of convenience and is not to be considered as limiting.

As stated above, a disadvantage associated with the prior art cutting device 10 shown in FIG. 1 is that it is limited by the singular relative rotational motion of the blades 14, 16. Thus, the cutting motion of the cutting device 10 cannot approximate the slicing motion of a surgeon's scalpel.

As shown in FIG. 1A, a result of the above-mentioned disadvantage is that there is a tendency for the work piece 12 to roll as is generally designated at 20. As the blades 14, 16 are pivoted about pivot point 18 (FIG. 1), the independent input forces F applied by each blade 14, 16, respectively, causes the work piece 12 to roll as indicated by arrow 22. The rolling of the work piece 12, in turn forces the blades 14, 16 to separate as generally designated at 24. Such blade separation impedes straight cutting and can lead to tearing of the work piece 12.

Some conventional surgical cutting devices also use large preloads on the blades to prevent rolling of the work piece which induces blade separation. The force required to overcome such preloads is frequently much greater than the force required to cut. This causes tactile feedback from cutting to fall well below a surgeon's perception threshold.

Figure 2:
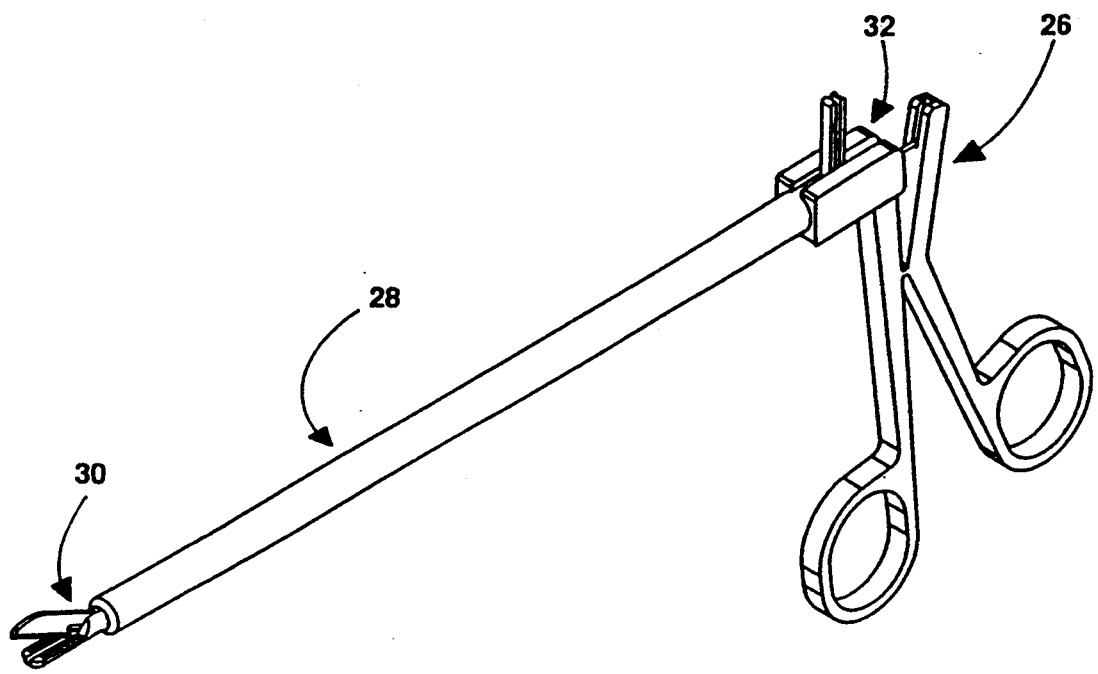
FIG. 2 is a perspective view of a compound motion cutting device in accordance with a preferred embodiment of the present invention.

Referring now to FIGS. 2-6, there is shown a first preferred embodiment of the compound motion cutting device, generally designated 26, in accordance with the present invention. As shown in FIG. 2, the compound motion cutting device 26 comprises an elongated center portion generally designated 28, a cutting end generally designated 30, and an operating end generally designated 32.

Figure 3:
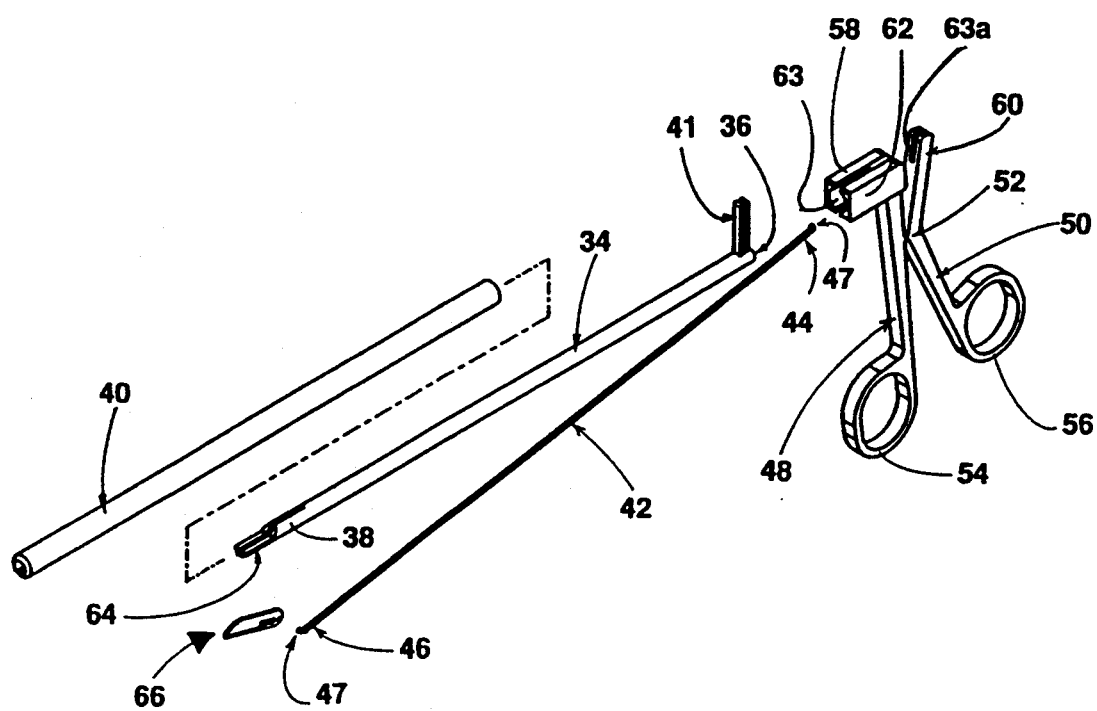
FIG. 3 is an exploded perspective view of the compound motion cutting device shown in FIG. 2.
Figure 4:
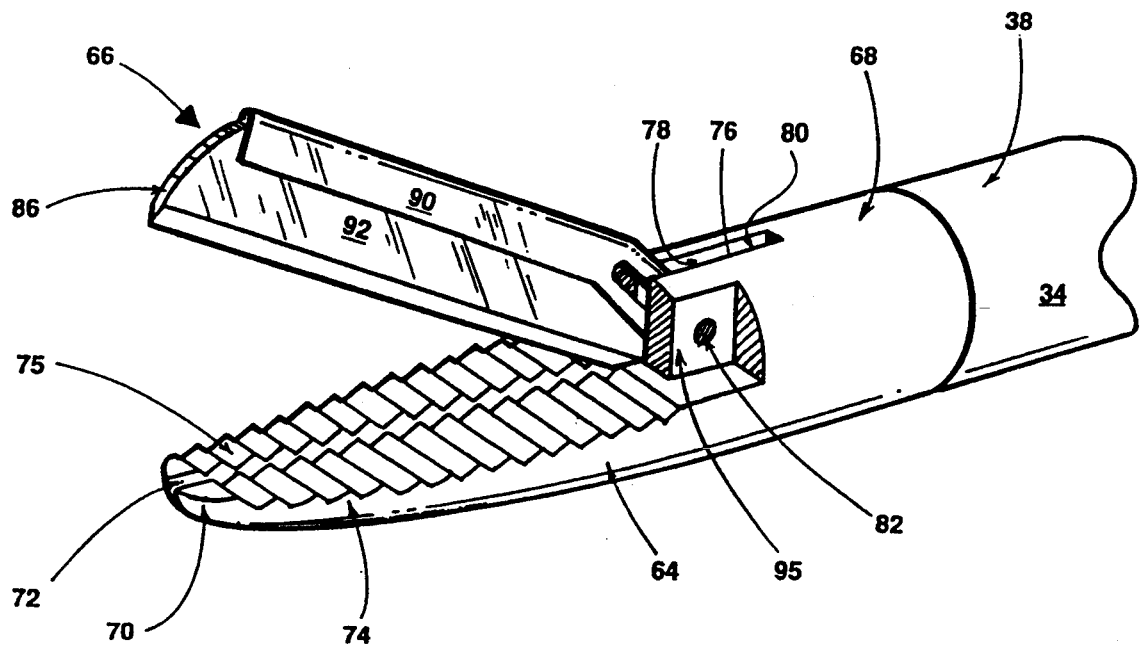
FIG. 4 is an enlarged perspective view of the cutting end of the compound motion cutting device shown in FIG. 2.

Referring now to FIGS. 2 and 3, the center portion 28 comprises a generally elongated tubular support member 34 having first and second ends 36, 38. A tubular insulator 40 is disposed around the tubular member 34. The first end 36 of the tubular member 34 includes a flange or detent 41 for inhibiting relative rotation of the tubular member 34 with respect to the operating end 32 as further described below. A drive rod 42 having first and second ends 44, 46 extends longitudinally into the tubular member 34 and extends slightly beyond each end 36, 38 of the tubular member 34.

In the present embodiment, the tubular member 34 is preferably formed of a high strength light weight material or structure, such as aluminum, steel, or a high strength polymer, the drive rod 42 is preferably formed of a similar material and the insulator 40 is formed of an electrical insulating material such as a shrink wrap plastic. However, it is understood by those skilled in the art that other materials and fabrication methods for the tubular member 34, the drive rod 42 and the insulator 40 are suitable. For example, the tubular member 34 could be injection molded from a suitable polymeric material, such as a hard plastic, the drive rod 42 could be formed of a high strength aluminum alloy or stainless steel and the insulator 40 could be injection molded from an electrically insulating plastic material such as polypropylene or polycarbonate.

As shown in FIG. 3, the operating end 32 preferably comprises a pair of handles or operating members 48, 50 of a type well known in the art and which are movable relative to each other about a common pivot point 52. First or distal ends of the operating members 48, 50 are provided with finger loops 54, 56, respectively, for receiving the finger of a user in a manner well known in the art. The second ends of the operating members 48, 50 are provided with connecting portions 58, 60, respectively. Preferably, the connecting portion 60 comprises a generally rectangular base member 62 having a slotted opening 63 fixed to the second end of the operating member 48. Preferably, the connecting portion 60 comprises a U-shaped groove 63a formed integrally with the second end of the operating member 50. However, it is understood by those skilled in the art that other forms of connecting portions 58, 60 are suitable for the second ends of the operating members 48, 50, respectively.

In the present embodiment, the operating end 32 is preferably formed of a high strength light weight material, such as aluminum, steel, or a high strength polymer. However, it is understood by those skilled in the art that other materials which provide for a rigid operating end structure could be used without departing from the spirit and scope of the invention. It is also understood that operating members 48, 50 could be pivoted with a pivoting pin without intersecting with each other. Additionally, the operating end 32 may be of the type disclosed in U.S. Pat. Nos. 4,712,545, 4,896,678, 5,152,780, 5,171,256 which are hereby incorporated by reference.

As best shown in FIG. 3, the first end 36 of the tubular member 34 and a corresponding end portion of the insulator 40 preferably extend longitudinally into the slotted opening 63 of the base member 62 with a tight fit. A suitable adhesive may be used to secure the tubular member 34 to the base member 62. The detent 41 preferably protrudes transversely from the slotted opening 63 and cooperates with the opening 63 to prevent relative rotation between the tubular member 34 and the base member 62. However, it is understood by those skilled in the art that other forms of connections, such as a press fit or a crimping connection, which would prevent relative rotation between the tubular member 34 and the base member 62, could be used without departing from the spirit and scope of the invention.

The drive rod 42 extends through the tubular member 34 with sufficient clearance to permit relative longitudinal movement therein. The first end 44 of the drive rod 42 also extends through the slotted opening 63 and into the U-shaped groove 63a to permit relative longitudinal movement therein. A retaining member 47 on the first end 44 of the rod secures the first end 44 of the drive rod 42 to the second end of the operating member 50. Preferably, the retaining member 47 is an oversized pin formed integrally with or secured to the first rod end 44. However, it is understood by those skilled in the art that any other means suitable for retaining the first rod end 44 to operating member 50 may be employed.

Referring now to FIGS. 3–6, the cutting end 30 according to the present embodiment comprises an anvil 64 supported proximate the second end 38 of the tubular member 34 and a cutting member generally designated 66. The anvil 64 according to the present embodiment is best described with reference to FIGS. 4–6. The anvil 64 preferably comprises a first end 68 secured to or integral with the second end 38 of the tubular member 34 and a second or distal end 70. The anvil 64 further includes a generally flat support surface 74 for supporting a work piece (not shown) to be cut. The first anvil end 68 includes a longitudinal groove 76 defined by two generally parallel sidewalls 78, 80 supporting a laterally extending generally cylindrical shaped pin 82. An elongated slot 72 extends generally longitudinally through the support surface 74.

Preferably, the anvil 64 is injection molded as a separate piece from a high strength polymer which can be secured to the second end 38 of the tubular member 34 during assembly with a friction fit, a snap-fit, a suitable adhesive or some other type of standard hardware. However, it is understood by those skilled in the art that other materials and fabrication methods are suitable for the anvil 64. For example, the anvil 64 could be formed integrally with the tubular member 34. Additionally, the anvil 64 could be injection molded from a transparent or translucent plastic material, such as acrylic, polycarbonate or crystal styrene, for improving visibility of a work piece being cut as further described below.

According to the present embodiment, the anvil support surface 74 is provided with a retention element for retaining a work piece (not shown) on the anvil surface 74 and preventing the work piece from being pulled into the anvil slot 72 by the cutting member 66 as further described below. Preferably, the retention element is a supporting toothed surface 75. However, it is understood by those skilled in the art that other types of retention elements, such as a releasable adhesive, which holds the work piece in place on the support surface 74 and prevents the work piece from being pulled into the anvil slot 72 could be used without departing from the spirit and scope of the invention. Alternatively, the support surface 74 could be a smooth flat surface.

Figure 5:
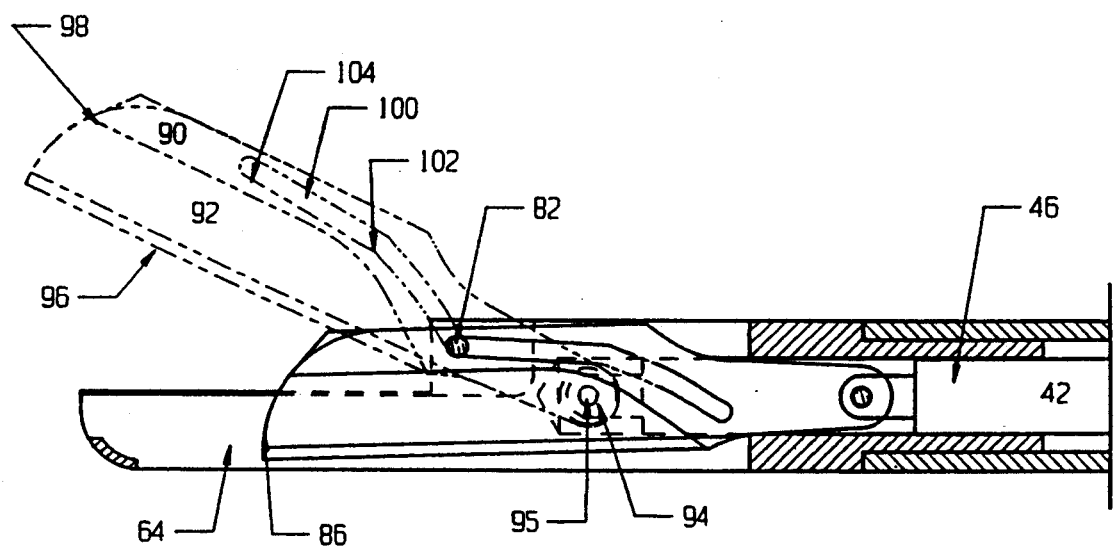
FIG. 5 is a side elevational view of the cutting device shown in FIG. 2 illustrating, in cross-section, the cutting member in the open and closed positions.
Figure 6:
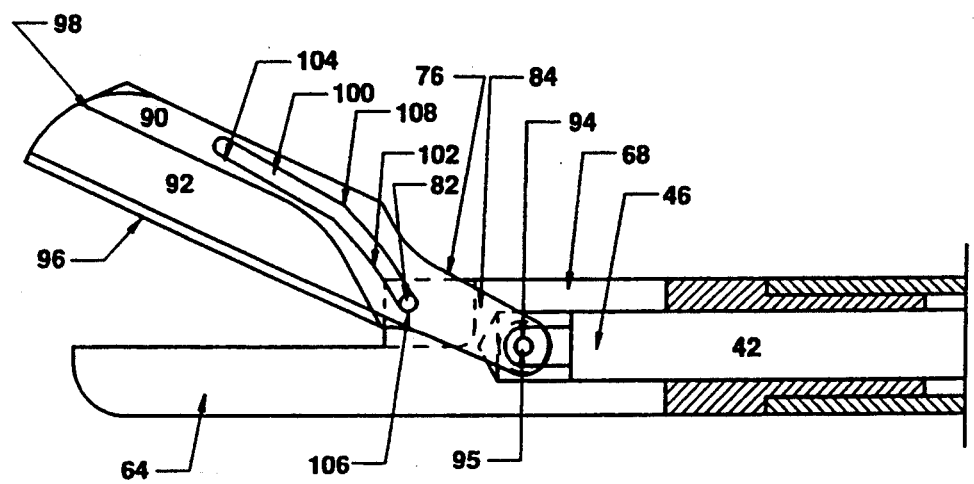
FIG. 6 is a side elevational view of the cutting device as shown in FIG. 2 illustrating, in cross-section, the cutting member in the open position.

As best shown in FIGS. 5 and 6, the cutting member 66 according to the present embodiment comprises a first end 84 and a second end 86. The first end 84 is pivotally attached by a retaining member 47 to the drive rod second end 46 and extends longitudinally into the groove 76 proximate the first end 68 of the anvil 64. The cutting member 66 is aligned with the anvil slot 72. A gripping member 90 extends from the first end 84 to the second end 86 of the cutting member 66. The gripping member 90 releasably secures a blade 92 at the second end 86 and is pivotally attached to the retaining member 47 at the first end 84.

Preferably, an opening 94 extends through the gripping member 90 at the first end 82 and the retaining member 47 is in the form of a pin in snap fit connection with the opening 94 to define a pivot joint 95 between the gripping member 90 and the second end 46 of the drive rod 42. However, it is understood by those skilled in the art that other forms of pivotal connections which allow relative pivoting between the gripping member 90 and the drive rod second end 46 are suitable. It also understood by those skilled in the art that the location of the pivot joint 95 could be varied along the gripping member 90 at the second end 86 of the cutting member 66 and/or along the drive rod second end 46 in order to adjust the motions of the blade 92 and the related cutting angles with respect to a work piece being cut.

Preferably, the gripping member 90 is channel-shaped in cross-section and the blade 92 includes a cutting edge 96 and a non-cutting edge 98 releasably secured within the channel of the gripping member 90 with a press fit. However, it is understood by those skilled in the art that other forms of connections between the gripping member 90 and blade 92 are suitable. For example, the blade 92 could be releasably secured to the channel of the gripping member 90 with a releasable adhesive or standard hardware, such that the blade 92 may be readily replaced, without departing from the spirit and scope of the invention. Additionally, the gripping member 90 need not be channel-shaped in cross-section, but could instead be planar in shape with opposite sides and the non-cutting edge 98 of the blade 92 could be releasably secured to a side of the gripping member 90 with any of the above-described forms of connections.

Preferably, the blade 92 is a thin generally straight edged blade having a predetermined thickness and the anvil slot 72 has a width which is at least slightly greater than the predetermined thickness of the blade 92 providing minimal clearance for the blade 92 as the blade moves at least partially into the anvil slot 72 (FIG. 5) during a cutting operation as further described below. Thus, blade preload friction is substantially reduced over prior art cutting devices, resulting in optimal cutting performance and tactile feedback. However, it is understood by those skilled in the art that other configurations are suitable for the blade 92. For example, the blade 92 could be other than a straight edged blade, such as a curve edged blade, for the purpose of adjusting the cutting motions of the blade 92 and the related work piece cutting angles for specific applications.

Preferably, the gripping member 90 is formed of aluminum, steel, or a high strength polymer and the blade 92 is formed of a suitable metal, such as stainless steel. However, it is understood by those skilled in the art that other materials are suitable for the gripping member 90 and blade 92. For example, the gripping member could be injection molded from a suitable polymeric material as described above for the anvil 64 and the blade 92 could be formed of aluminum.

Referring now to FIGS. 5 and 6, the cutting member 66 of the present embodiment further includes a slot 100 having a predetermined profile and extending laterally through the gripping member 90. Preferably, the profile of the slot 100 is cammed, including first and second sections 102, 104 defining first, second and third pin positions 106, 108, 110, respectively. The pin 82, located within the groove 76 of the anvil 64, extends through the cam slot 100 and has an outer diameter at least slightly less than the predetermined width of the cam slot 100. In this manner the cutting member 66 can be translated in a longitudinal direction relative to the tubular member 34 to position the pin 82 from the first position 106, through the second position 108 to the third position 110 as further described below. It is also preferred that the first section 102 have a first predetermined curvature and the second section 104 have a second predetermined curvature which is greater or steeper than the first predetermined curvature. However, it is understood by those skilled in the art that other profiles are suitable for the slot 100. For example, the slot 100 could comprise only a single section with a continuous curvature or more than one section with identical or different curvatures. It is also understood by those skilled in the art that the number of curve sections within the slot 100 and the respective degree of curvatures of the sections may be adjusted in order to achieve varying degrees of blade motion and related cutting angles for specific applications.

The operation of the compound motion cutting device 26 of the present embodiment will be described with reference to FIGS. 2–6. When the finger loops 54, 56 are moved toward each other (not shown), the drive rod 42 is moved in a first, rearward, longitudinal direction within the tubular member 34 towards the operating end 32. The movement of the drive rod 42 in the first direction causes the cutting member 66 to also move in the first direction and the pin 82 to traverse the cam slot 100 from the first position 106, through the second position 108 to the third position 110 thereby causing the cutting member 66 to simultaneously rotate toward the anvil 64 and to extend at least partially into the anvil slot 72 (FIG. 5) to cut a work piece (not shown) positioned on the anvil support surface 74 with a combined longitudinal and a rotational slicing motion. Thus, the cutting device of the present embodiment effects a more efficient slicing motion over prior art cutting devices that more closely approximates the motion of a surgeon's scalpel.

When the finger loops 54, 56 of the operating members 48, 50, respectively, are subsequently spread apart (FIG. 2), the drive rod 42 is moved in an opposite, second longitudinal direction within the tubular member 34 away from the operating end 32. The movement of the drive rod 42 causes the cutting member 66 to move in the second longitudinal direction and the pin 82 to traverse the cam slot 100 from the third position 110, through the second position 108 to the first position 106 to cause the cutting member 66 to rotate away from the anvil 64 and out of the anvil slot 72. The compound motion cutting device 26 is then ready for another slicing operation by repeating the above-mentioned steps.

It is understood by those skilled in the art and from the above description of a preferred first embodiment of the present invention that the motion of the blade 92 and related cutting angle may be determined and adjusted by one of the following independent variables in order to achieve specific cutting applications: (1) the relative movement of the operating members 48, 50; (2) the location of the pivot joint 95 relative to the cutting member 66; (3) the profile of the cam slot 100; (4) the configuration of the blade 92; and (5) the configuration of the anvil 64.

Figure 7:
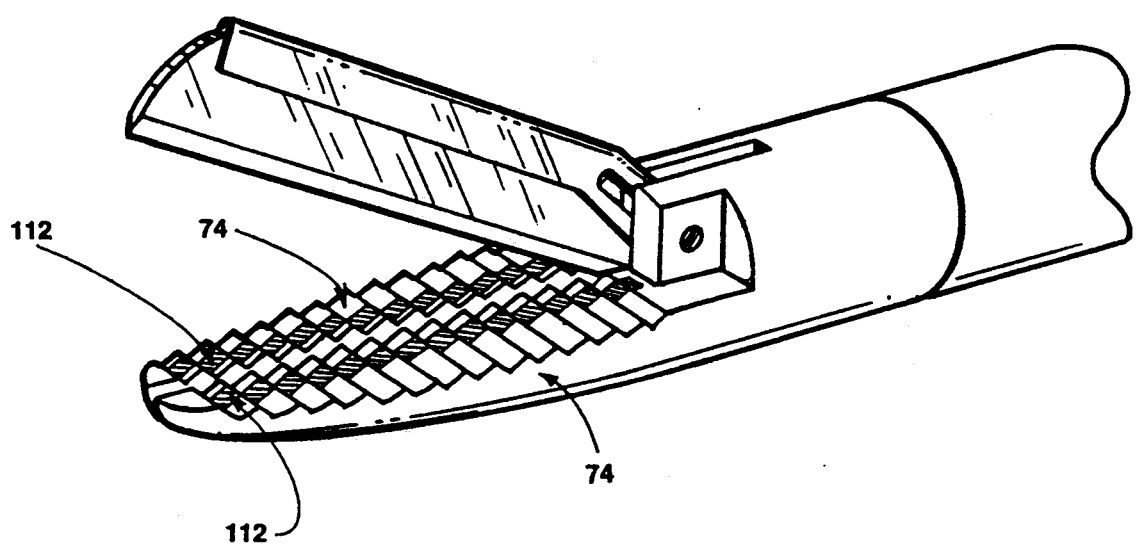
FIG. 7 is an enlarged perspective view of a second preferred embodiment of the compound motion cutting device in accordance with the present invention.

A compound motion cutting device according to a second embodiment, as shown in FIG. 7, includes the essential elements of the compound motion cutting device previously described with reference to FIGS. 2–6. However, the cutting device of the second embodiment is a bipolar single bladed design adapted for electrocautery and microcautery surgical operations as further described below.

As shown in FIG. 7, the blade 92 of the second embodiment constitutes a first electrode, with a size and shape which can be varied to meet particular surgical requirements. For example, microcautery requires the first electrode 92 to be very thin. The gripping member 90, the drive rod 42 and the tubular member 34 are preferably formed from a suitable electrically insularire material, such as a polymer. However, it is understood by those skilled in the art that other materials which are not electrically conductive, are suitable.

In the present embodiment, the anvil support surface 74 is provided with a pair of elongated strips 112, which separately or together defining a second electrode. The anvil 64 is preferably made of a suitable, high strength polymer with inherent insulation characteristics, such as a hard plastic. However, it is understood by those skilled in the art that other materials with insulation characteristics, such as polypropylene or polycarbonate, are suitable for the anvil 68. The strips 112 may be made of any of the electrically conductive materials discussed above with reference to the first electrode 92.

In the present embodiment, electrical current is delivered to the first and second electrodes 92, 112 through electrical leads (not shown) preferably running through the tubular member 34. The electrical leads are connected to an appropriate bipolar cutter/coagulator device (not shown). Details of the electrical leads and bipolar cutter/coagulator device are not pertinent to the present invention and are well understood by those skilled in the art. Accordingly, further description thereof is omitted for purposes of convenience only and is not limiting.

The operation of the compound motion cutting device according to the second embodiment is essentially the same as the operation described above with reference to FIGS. 2–6. However, in addition to physical cutting, the electrodes 92, 112 function with the bipolar cutter/coagulator device to provide electrical cutting and/or coagulation as deemed by a user.

From the foregoing description, it can be seen that the present invention comprises an improved compound motion cutting device. It will be appreciated by those skilled in the art, that changes could be made to the embodiments described in the foregoing description without departing from the broad inventive concept thereof. It is understood, therefore, that this invention is not limited to the particular embodiment disclosed, but is intended to cover all modifications which are within the scope and spirit of the invention as defined by the appended claims.

We claim:

1. A compound motion cutting device comprising:
   (a) a tubular member having first and second ends;
   (b) a pair of operating members movable relative to each other, one of the operating members being secured to the first end of the tubular member;
   (c) a drive rod having first and second ends and extending longitudinally into the tubular member, the first end of the rod being secured to the other of the operating members such that movement of the operating members relative to each other causes the rod to move longitudinally within the tubular member;
   (d) an anvil supported proximate the second end of the tubular member, the anvil having a predetermined configuration including a surface for supporting a work piece and a slot extending through the support surface;
   (e) a cutting member having first and second ends, the first end of the cutting member being pivotally attached to the second end of the drive rod for movement therewith, the cutting member being aligned with the anvil slot and including a cam slot with a predetermined profile extending laterally therethrough; and (f) a pin supported proximate the second end of the tubular member, the pin extending through the cam slot in the cutting member, whereby movement of the operating members relative to each other in one direction causes the drive rod to move in a first longitudinal direction within the tubular member toward the operating members, the movement of the drive rod in the first direction causing the cutting member to move in the first direction, the pin and the cutting member cam slot cooperating to cause the cutting member to simultaneously rotate toward the anvil and to extend at least partially into the anvil slot to cut the work piece at a predetermined cutting angle relative to the anvil surface with a combined longitudinal and rotational slicing motion.

2. The cutting device as set forth in claim 1, whereby the cutting member comprises a gripping member and a blade having a predetermined configuration, the blade being releasably secured to the gripping member.

3. The cutting device as set forth in claim 2, wherein the anvil surface is provided with a retention element for retaining the work piece on the support surface and for preventing the work piece from being pulled into the anvil slot by the blade when the blade moves at least partially into the anvil slot to cut the work piece.

4. The cutting device as set forth in claim 3, wherein the retention element is a supporting toothed surface.

5. The cutting device as set forth in claim 3, wherein the retention element is a releasable adhesive on the support surface.

6. The cutting device as set forth in claim 2, wherein the blade is of a predetermined lateral thickness and the lateral width of the anvil slot is greater than the predetermined blade thickness.

7. The cutting device as set forth in claim 6, wherein the cutting member cam slot has a curved profile.

8. The cutting device as set forth in claim 7, wherein the curved cam slot comprises first and second sections, the first section having a first predetermined curvature and the second section having a second predetermined curvature greater than the first predetermined curvature.

9. The cutting device as set forth in claim 8, wherein the movement of the cutting member and the predetermined cutting angle is determined by at least one of the relative movement of the operating members, the location of the pivotal attachment between the first end of the cutting member and the second end of the drive rod, the cutting member cam slot profile, the configuration of the anvil and the configuration of the blade.

10. The cutting device as set forth in claim 1, wherein the cutting member cam slot has a curved profile.

11. The cutting device as set forth in claim 10, wherein the curved cam slot comprises first and second sections, the first section having a first predetermined curvature and the second section having a second predetermined curvature greater than the first predetermined curvature.

12. The cutting device as set forth in claim 2, wherein the blade comprises a first electrode and the anvil includes a second electrode such that upon attachment to a bipolar generator, the cutting device may be employed as a bipolar cutter or coagulator.

13. The cutting device as set forth in claim 12, wherein the second electrode comprises a pair of conductive strips supported on the anvil surface on both lateral sides of the anvil slot.

14. A compound motion cutting device comprising:
a support member;
an anvil supported by the support member, the anvil having a predetermined configuration including a surface for supporting a work piece and a slot extending through the support surface;
a cutting member aligned with the anvil slot and including a cam slot with a predetermined profile extending laterally therethrough; and
a pin supported by the support member, the pin extending through the cam slot in the cutting member,
whereby longitudinal movement of the cutting member in a first direction relative to the support member results in the pin and the cutting member cam slot cooperating to cause the cutting member in a rotate toward the anvil and to extend at least partially into the anvil slot to cut the work piece at a predetermined cutting angle relative to the anvil surface with a combined longitudinal and rotational slicing motion.

* * * * *